United States Patent
Mathieu et al.

(10) Patent No.: US 10,451,493 B2
(45) Date of Patent: Oct. 22, 2019

(54) SYSTEM COMPRISING A CELLULAR NETWORK OF CAPACITIVE PRESSURE AND SHEAR-STRESS SENSORS AND MANUFACTURING PROCESS

(71) Applicant: FEETME, Versailles (FR)

(72) Inventors: Alexis Mathieu, Bonneuil-Matours (FR); Julien Mercier, Bourges (FR)

(73) Assignee: FEETME, Versailles (FR)

( * ) Notice: Subject to any disclaimer, the term of this patent is extended or adjusted under 35 U.S.C. 154(b) by 106 days.

(21) Appl. No.: 15/327,196

(22) PCT Filed: Jul. 16, 2015

(86) PCT No.: PCT/FR2015/051947
§ 371 (c)(1),
(2) Date: Jan. 18, 2017

(87) PCT Pub. No.: WO2016/009151
PCT Pub. Date: Jan. 21, 2016

(65) Prior Publication Data
US 2017/0176266 A1    Jun. 22, 2017

(30) Foreign Application Priority Data
Jul. 18, 2014 (FR) .................................... 14 56955

(51) Int. Cl.
*G01L 1/14* (2006.01)
*A61B 5/103* (2006.01)
(Continued)

(52) U.S. Cl.
CPC ............ *G01L 1/142* (2013.01); *A43B 3/0005* (2013.01); *A43B 17/00* (2013.01); *A61B 5/1036* (2013.01);
(Continued)

(58) Field of Classification Search
CPC ......... G01L 3/106; G01L 1/142; G01L 1/146; G01L 5/165; G01L 1/00; G01L 1/2287;
(Continued)

(56) References Cited

U.S. PATENT DOCUMENTS 4,644,801 A * 2/1987 Kustanovich ........... G01L 1/146
361/283.1
4,827,763 A * 5/1989 Bourland ................ A61B 5/113
361/283.1
(Continued)

FOREIGN PATENT DOCUMENTS

EP    2 607 876 A1    6/2013
FR    2 878 956 A1    6/2006
FR      2878956    *  6/2006

OTHER PUBLICATIONS

International Search Report, dated Oct. 12, 2015, from corresponding PCT application.

*Primary Examiner* — Octavia Hollington
(74) *Attorney, Agent, or Firm* — Young & Thompson

(57) ABSTRACT

Disclosed is a system and to a process for manufacturing a system including a network of sensors including a sheet of dielectric material that is elastically deformable under compressive and shear stress, each cell of the network including a first capacitive sensor for sensing normal pressure in a first direction, a second capacitive sensor for sensing shear stress in a second direction and a third capacitive sensor for sensing shear stress in a third direction. Each capacitive sensor includes a first electrode fixed to the first side of the sheet of dielectric material and a second electrode fixed to the second side of the sheet of dielectric material, the first electrodes of the capacitive sensors of a given cell being connected in series to a first electrically conductive track connecting a row of cells of the network of sensors.

13 Claims, 6 Drawing Sheets

(51) Int. Cl.
  *G01L 5/16* (2006.01)
  *A43B 3/00* (2006.01)
  *A43B 17/00* (2006.01)
  *G01D 5/241* (2006.01)
  *G01L 1/00* (2006.01)
  *G01L 1/22* (2006.01)

(52) U.S. Cl.
  CPC ............ *G01D 5/2412* (2013.01); *G01L 1/146* (2013.01); *G01L 5/165* (2013.01); *G01L 1/00* (2013.01); *G01L 1/2287* (2013.01); *G01L 5/167* (2013.01); *G01N 2203/0025* (2013.01)

(58) Field of Classification Search
  CPC ......... G01L 5/167; G01L 1/04; A43B 3/0005; A43B 17/00; A43B 7/00; A43B 3/00; A61B 5/1036; A61B 5/103; G01D 5/2412; G01N 2203/0025; G06F 11/30; G06F 3/041
  USPC .................................................. 73/862.626
  See application file for complete search history.

(56) References Cited

U.S. PATENT DOCUMENTS

| | | | | |
|---|---|---|---|---|
| 5,010,772 | A * | 4/1991 | Bourland | ............... A61B 5/113 73/172 |
| 5,449,002 | A | 9/1995 | Goldman | |
| 6,505,522 | B1 * | 1/2003 | Wilssens | ............. A61B 5/1036 73/862.51 |
| 6,826,968 | B2 * | 12/2004 | Manaresi | ................ B63H 9/06 73/862.046 |
| 7,343,813 | B1 | 3/2008 | Harrington | |
| 7,719,007 | B2 * | 5/2010 | Tompkins | ............... G01L 1/142 257/48 |
| 8,250,926 | B2 | 8/2012 | Yang et al. | |
| 9,904,393 | B2 * | 2/2018 | Frey | ...................... G06F 3/0414 |
| 2006/0267140 | A1 | 11/2006 | Lee et al. | |
| 2013/0093437 | A1 | 4/2013 | Koo et al. | |
| 2014/0076066 | A1 | 3/2014 | Harrington et al. | |

* cited by examiner

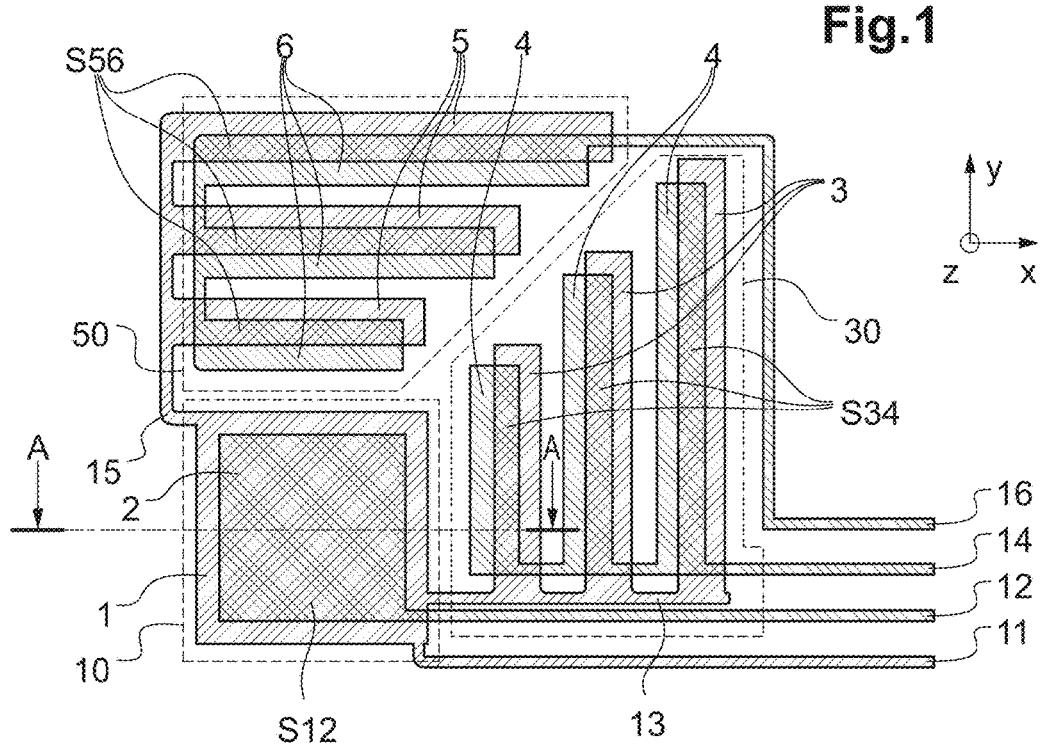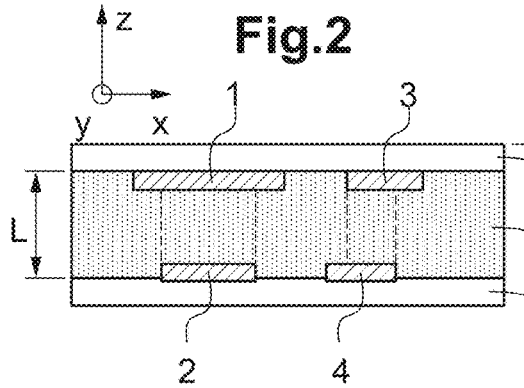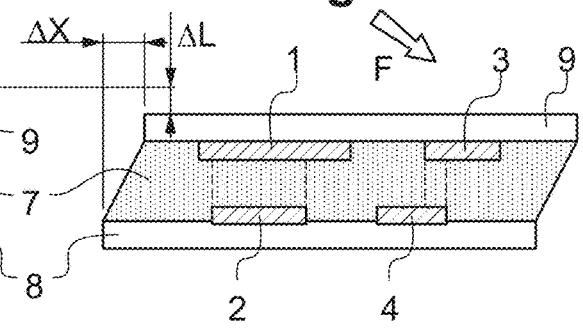

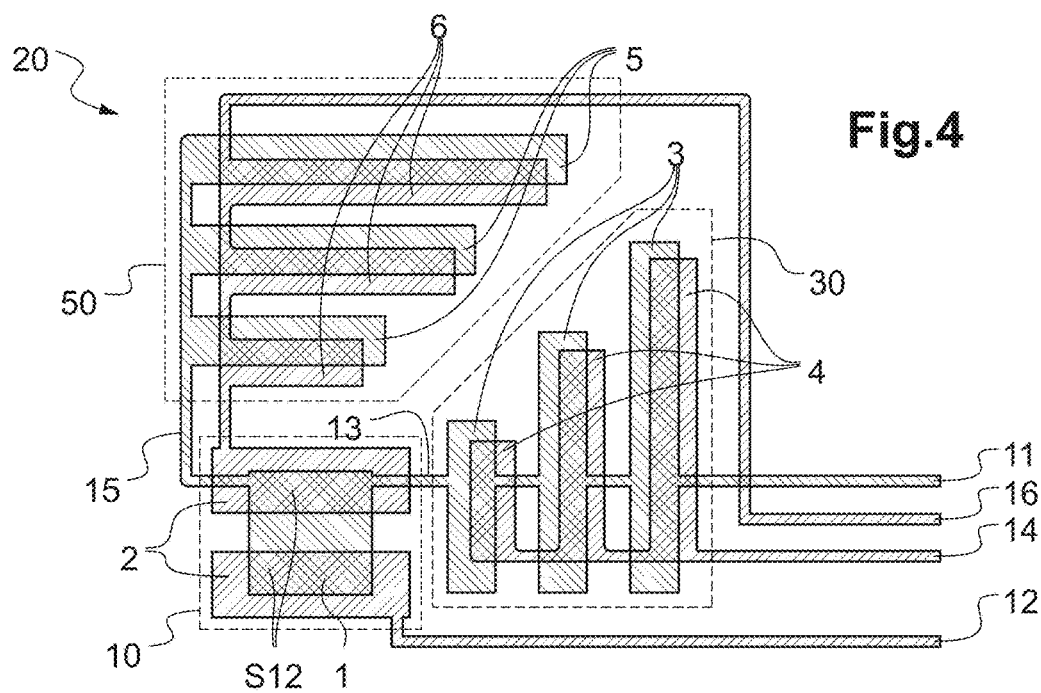
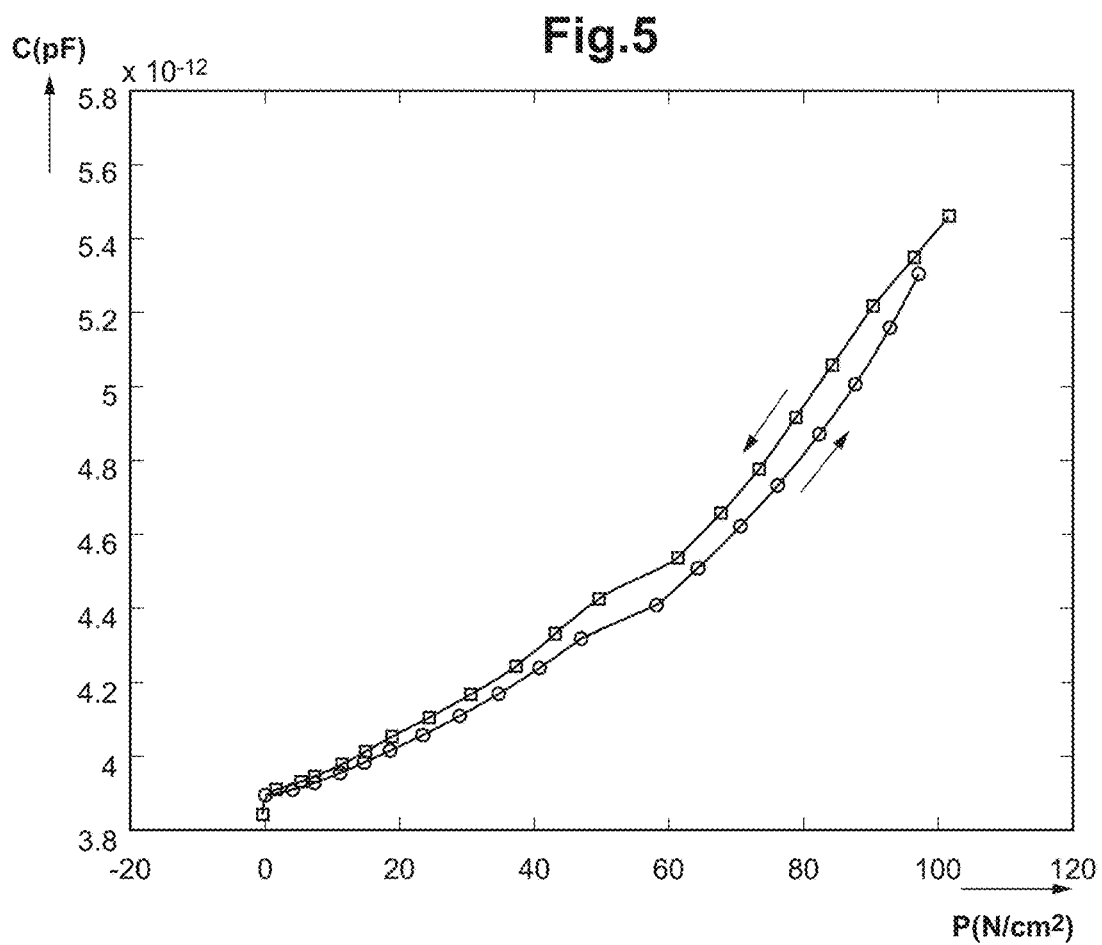

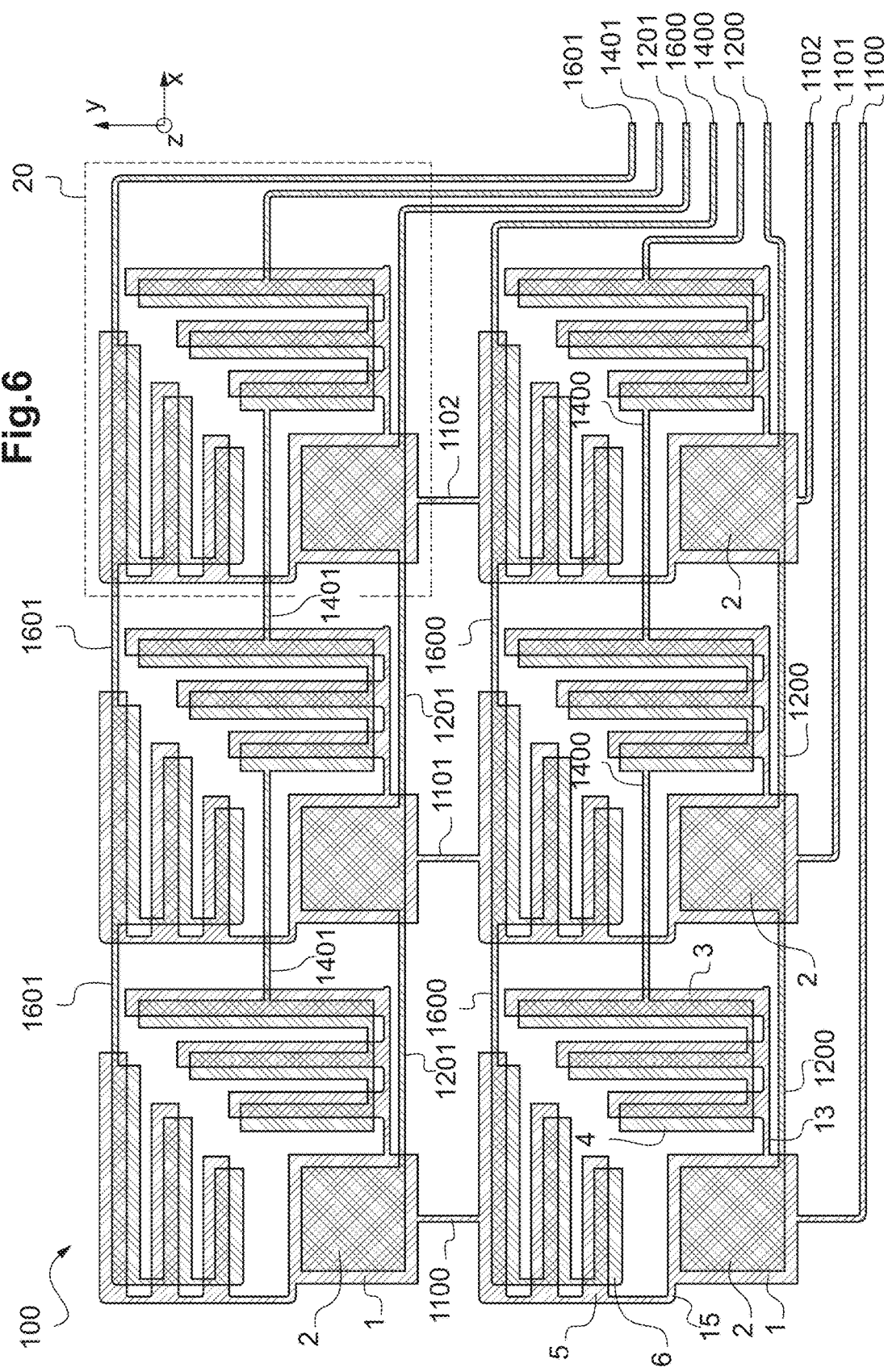

SYSTEM COMPRISING A CELLULAR NETWORK OF CAPACITIVE PRESSURE AND SHEAR-STRESS SENSORS AND MANUFACTURING PROCESS

TECHNICAL FIELD

The present invention relates to a sensor network system for measuring pressure forces with a high spatial resolution. A pressure force can generally be broken into, on the one hand, a compressive force that is applied perpendicular to the surface of the pressure sensor, and on to the other hand, a shear force that is applied in an oblique direction with respect to the surface of the pressure sensor.

More precisely, the invention relates to a sole with pressure sensors intended to measure compressive and shear forces with a high spatial resolution. The invention also relates to various methods of manufacturing a pressure sensor network system.

TECHNOLOGICAL BACKGROUND

In the medical field or the sport field, it is desirable to know the distribution of the pressure forces exerted by the feet of a person, in static or dynamic position. In the medical field, a sole with pressure sensors finds applications as a diagnostic sole in podology or orthopedics. Daily worn by a diabetic patient suffering from neuropathy, a sole with pressure sensors may allow improving the prevention of foot lesions. In the sport field, a sole with pressure sensors, worn by a sportsman and connected to a smartphone, allows the sportsman to quantify his running. Analyzing the distribution of the pressure forces applying in particular at the foot sole during walking, running or jumping may allow the sportsman to consciously correct a postural unbalance in order to avoid the occurrence of pains or injuries.

There exist devices with pressure sensors based on optical, magnetic or electrical technologies, and in particular with resistive sensors, inductive sensors (see EP 2607876) or capacitive sensors (see U.S. Pat. No. 7,343,813, US2014/076066).

An advantage of the capacitive pressure sensors is to be little sensitive to the temperature variations.

A capacitive pressure sensor includes at least two electrodes separated by a dielectric material. The electrical capacitance of a capacitive sensor is given by the formula of a capacitor between two plates:

$$C = \frac{\varepsilon \cdot S}{L} \quad (I)$$

where C represents the electrical capacitance of the capacitive sensor, of the capacitor type, S the surface of the electrodes placed opposite to each other, L the distance between the two electrodes and $\varepsilon$ the dielectric constant of the material between the electrodes.

Under the effect of a normal pressure force, the variation of thickness L of the dielectric material produces an inversely proportional variation of the electrical capacitance C of the sensor.

It is known for example from the document U.S. Pat. No. 5,449,002 a capacitive pressure sensor based on a resilient polyurethane dielectric in sandwich between two electrical conductors. The variation of the electrical capacitance of this sensor is almost linear as a function of the weight applied, which allows an easy detection. This sensor may be used as a shoe sole, a gripping handle or a support to measure the compressive forces in various medical equipments such as crutch, wheelchair, treadmill. However, such a sensor provides no pressure measurements spatially resolved on the surface of the sensor. Moreover, this capacitive pressure sensor does not allow discriminating a normal pressure from a pressure induced by a shear force.

Now, by application of the formula (I), under the effect of a shear force, a variation of the surface S of the opposite electrodes produces a proportional variation of the electrical capacitance of the sensor. In the case of an elastically deformable dielectric material, the variation of surface S induced by the shear force is generally accompanied with a variation of the thickness L. It is hence necessary to measure independently the variation of thickness to extract from the capacitance variation measurement a measurement of the variation of surface S, in order to deduce therefrom a measurement of the shear force.

Recently, different examples of multiple capacitive sensors have allowed discriminating the normal pressure measurement from the shear force measurement (see US 2013/0093437, U.S. Pat. No. 8,250,926). The capacitive pressure and shear sensors are used in particular in the field of touch screens, haptic interfaces, textiles integrating sensors.

However, the integration of a great number of capacitive pressure sensors to manufacture a high-spatial-resolution sensor network has for drawback to require a far greater number of electrical connections connecting the sensor network to the measurement system.

The document R. Supraneni, Q. Guo, Y. Xie, D. J. Young and C. H. Mastrangelo "A three-axis high-resolution capacitive tactile imager system based on floating comb electrodes", Journal of Micromechanics and Microengineering, 23 (2013) 075004, describes the design and the manufacturing of a high-spatial-resolution tactile imager for measuring the compressive and shear forces. The tactile imager includes a dielectric formed of a sheet of silicone polymer and a flexible printed circuit (FPCB). Each cell of the tactile imager includes two capacitors sensitive to displacements in a direction X and two capacitors sensitive to displacement in a direction Y. The four capacitors of a cell include, on one face of the dielectric, floating electrodes, and, on the other face of the dielectric, a FPCB supporting comb-shaped electrodes connected by two vertical electrical tracks and two horizontal electrical tracks. The electrical measurement of the four capacitors of a cell requires the multiplexed addressing of the vertical and horizontal electrical tracks, to provide normal pressure measurements in the direction Z, and shear measurements in the directions X and Y. Nevertheless, the horizontal and vertical electrical tracks being deposited on a same printed circuit, the method of manufacturing the printed circuit requires the superimposition of at least two levels of electrical tracks connected by interconnections or vias. A drawback of the method of manufacturing of the dual-level printed circuit is that it requires a greater number of steps of manufacturing. Moreover, this method requires a rigid printed circuit substrate, which may suit for tactile applications, but generally do not suit for an application to a sole with pressure sensors. Finally, the interconnections between two levels of electrodes deposited on a deformable substrate are fragile and may create electrical faults.

Contrary to the tactile applications in which the substrate is generally rigid and may be thick, a sole with pressure sensors must have both a small thickness, lower than a few to millimeters, and a very high flexibility. A sole with pressure sensors must support a pressure dynamics comprised between 0 and 15 kg/cm$^2$.

On the other hand, a drawback of the capacitive sensors based on deformable dielectric materials is that the deformation thereof generally shows hysteresis, liable to induce measurement errors.

Moreover, the capacitive shear-force sensors have a lower sensitivity than the normal pressure sensors. A capacitive shear-force sensor must generally extend over a greater surface than a capacitive normal-pressure sensor.

There thus exists a need for a system and a method allowing manufacturing a sensor network system for measuring pressure forces with a high spatial resolution, while having a small thickness and a great flexibility, in particular for the application to a sole with pressure sensors.

One of the objects of the invention is to propose a sensor network system for measuring pressure forces with a high spatial resolution, having a small thickness and a limited number of electrical connections. Another object of the invention is to provide not only compressive force measurements, but also shear force measurements.

Another object of the invention is to propose a sensor network system that suits for soles in the medical, sport or entertainment field.

Another object of the invention is to propose a simple, rapid and cheap method of manufacturing, allowing manufacturing a high-resolution capacitive sensor network system.

OBJECT OF THE INVENTION

The present invention has for object to remedy the drawbacks of the prior art techniques and relates to a pressure, and possibly shear, sensor network system, comprising a sheet of dielectric material elastically deformable in compression and shear, the sheet of dielectric material having a first face and a second face, a network comprising a plurality of pressure sensor cells, the cells being arranged in at least three rows and at least three columns, each cell comprising a first capacitive sensor for sensing normal pressure in a first direction.

According to the invention, each capacitive sensor is consisted of a first electrode fixed to the first face of the sheet of dielectric material and a second electrode fixed to the second face of the sheet of dielectric material, said first electrode of the capacitive normal-pressure sensor of a cell being connected in series to a first electrically conductive track connecting a row of cells of the sensor network; the second electrode of the capacitive normal-pressure sensor of a cell being connected to a second electrically conductive track connecting a column of capacitive normal-pressure sensors of the sensor network and the sensor network system comprises addressing means adapted to measure the electrical capacitance of a capacitive sensor located at the intersection of a row and a column, said row corresponding to a first track connected to said first electrode and said column corresponding to another track connected to one of said second electrodes.

The sensor network system hence allows measuring with a high spatial resolution the spatial distribution of the force vectors applied to the sensor network. The architecture of the system allows providing measurements of a great number of sensors via an extremely reduced number of electrical connections.

The advantages of this sensor network system are its small thickness, the spatial density of the measurements, as well as the ability of the system to measure friction forces.

Moreover, the capacitive sensors are little sensitive to the variations of temperature and essentially sensitive to the mechanical effects.

In a particular and advantageous embodiment, the sheet of dielectric material elastically deformable in compression and shear is a material chosen among: a natural matter such as cork, or an elastomer of natural origin, as for example a rubber, or a synthetic elastomer, in particular a urethane, a silicone, a butyl rubber, a polymer, a neoprene, a polyurethane or a polyisoprene. Advantageously, the sheet of dielectric material is in the form of a foam (for example, an elastomeric foam, in particular urethane foam) or of a micro-architectured material (for example, cork).

In a particular embodiment, said first electrode and said first electrically conductive track are printed on a sheet of electrically insulating and flexible material, and, respectively, said second electrode and said other electrically conductive tracks are printed on another sheet of electrically insulating and flexible material.

According to a preferred embodiment, the first electrically conductive track and the second electrically conductive track of a cell are connected to an electronic system adapted to measure a variation of the electrical capacitance of the capacitive normal-pressure sensor, the electronic system being adapted to deduce therefrom a normal pressure force applied to said capacitive normal-pressure sensor along the first direction.

Advantageously, at least one cell of the sensor network comprises a second capacitive sensor for sensing shear in a second direction and a third capacitive sensor for sensing shear in a third direction, each capacitive shear sensor being consisted of a first electrode fixed to the first face of the sheet of dielectric material and a second electrode fixed to the second face of the sheet of dielectric material, said first and second electrodes of the capacitive shear sensors being comb-shaped, said first electrodes of the capacitive sensors of a cell being connected in series, the second electrode of the capacitive sensor for sensing shear in the second direction being connected to a third electrically conductive track connecting a row of capacitive sensors for sensing shear in the second direction of the sensor network; and the second electrode of the capacitive sensor for sensing shear in the third direction being connected to a fourth electrically conductive track connecting a column of capacitive sensors for sensing shear in the third direction of the sensor network.

Complementarily, the first electrically conductive track and the third electrically conductive track of a cell are connected to said electronic system, which is adapted to measure a variation of the electrical capacitance of the second capacitive sensor for sensing shear force in the second direction, the electronic system being adapted to deduce therefrom the amplitude and direction of a shear force applied to said capacitive shear-force sensor along the second direction.

Advantageously, the first electrically conductive track and the fourth electrically conductive track of a cell are connected to said electronic system, which is adapted to measure a variation of the electrical capacitance of the third capacitive sensor for sensing shear in the third direction, the electronic system being adapted to deduce therefrom the amplitude and direction of shear force applied to said third capacitive shear sensor along the third direction.

In a particularly advantageous embodiment, said electrically conductive tracks are connected to means for measuring a variation of electrical capacitance of the capacitive sensors by wired or wireless links.

Advantageously, the pressure sensor network system comprises a device for displaying shear pressure force measurements, wherein the display device is configured to represent graphically, as a function of the arrangement of the sensor network, the normal pressure measured by each cell of the sensor network and simultaneously the amplitude and direction of the shear force measured by each cell of the sensor network.

The invention will find a particularly interesting application in the manufacturing of a shoe sole comprising a pressure sensor network system according to one of the embodiments described.

The invention also relates to a method of manufacturing a sole with a network of capacitive pressure sensor cells comprising a plurality of pressure sensor cells, the cells being arranged in at least three rows and at least three columns, the method comprising the following steps:

- printing by screen printing a first pattern of conductive electrodes on a first surface of a first material, the first pattern of conductive electrodes comprising, for each row of the sensor network, a first track connecting in series a row of cells of the sensor network;
- printing by screen printing a second pattern of conductive electrodes on another surface of the first material or of another material, the second pattern of conductive electrodes comprising, for each column of the sensor network, a second track connecting in series a column of cells of the sensor network;
- fixing the first surface carrying the first pattern of conductive electrodes to one face of a sheet of dielectric material elastically deformable in compression and shear;
- aligning the other surface carrying the second pattern of conductive electrodes with respect to the first pattern of conductive electrodes and fixing the other surface carrying the second pattern of conductive electrodes to the other face of said sheet of dielectric material, so as to form a network of capacitive pressure sensor cells.

Advantageously, the sole includes at least 48 pressure sensor cells.

This method of manufacturing allows integrating a great number of pressure sensors on an elastically deformable dielectric material, with a low cost of manufacturing. This method is to performed in a very small number of steps, and does not require an as high accuracy as a method of manufacturing printed circuits based on the conventional metallization techniques. The method of printing with metal ink avoids the use of liquid-phase chemical components.

In a particular embodiment, each cell of the sensor network comprises a second capacitive sensor for sensing shear in a second direction and a third capacitive sensor for sensing shear in a third direction, each capacitive shear sensor being consisted of a first electrode fixed to the first face of the sheet of dielectric material and a second electrode to the second face of the sheet of dielectric material, said first and second electrodes of the capacitive shear sensors being comb-shaped, said first electrodes of the capacitive sensors of a cell being connected in series, the first pattern of conductive electrodes comprises a first track connecting a row of cells, the first pattern of electrodes connecting in series the capacitive pressure and shear sensors of a same cell, and the second pattern of conductive electrodes comprises a second electrically conductive track connecting a column of capacitive normal-pressure sensor, a third electrically conductive track connecting a column of second capacitive sensors for sensing shear in the second direction and a fourth electrically conductive track connecting a column of third capacitive sensors for sensing shear in the third direction, so as to form a network of capacitive pressure and shear sensor cells having four electrically conductive tracks connected to each capacitive pressure and shear sensor cell.

The invention will find a particularly advantageous application in a sole with pressure sensors for applications in the medical, sport or entertainment field.

DETAILED DESCRIPTION OF AN EXEMPLARY EMBODIMENT

The present invention also relates to the characteristics that will be revealed in the following description and that will have to be considered in isolation or according to any technically possible combination thereof.

This description, given by way of non-limitative example, will allow a better understanding of how the invention may be performed in reference with the appended drawings, in which:

FIG. 1 schematically shows a top view of a capacitive pressure sensor cell according to an embodiment of the invention;

FIG. 2 schematically shows a sectional view along the line AA of the capacitive pressure sensor cell of FIG. 1;

FIG. 3 illustrates the capacitive pressure sensor cell of FIG. 2, subjected to a shear force applied in the direction of axis X;

FIG. 4 schematically shows a top view of a capacitive pressure sensor according to a variant of the invention;

FIG. 5 shows a measurement of normal pressure force by applying an increasing then decreasing pressure force, and illustrates the effect of hysteresis of the sensor;

FIG. 6 illustrates a top view of a network of capacitive normal-pressure and shear-force sensors;

Figure 7:
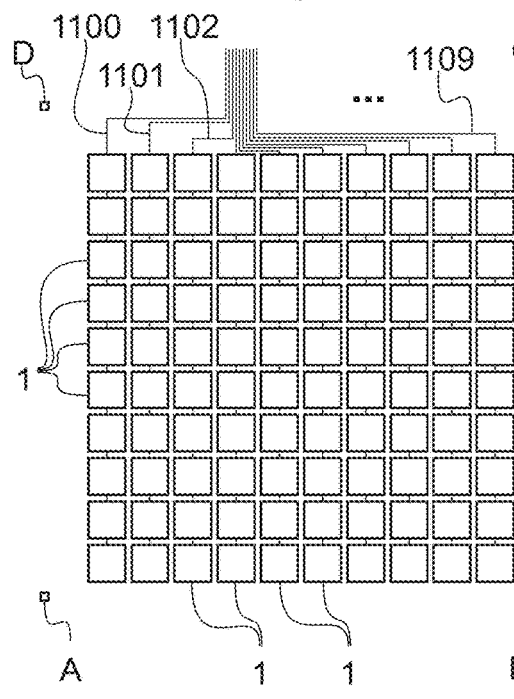
Figure 8:
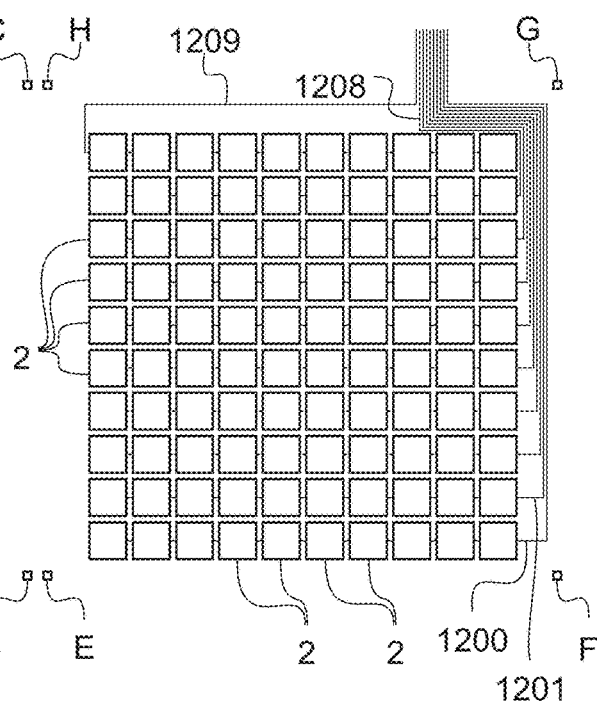
Figure 9:
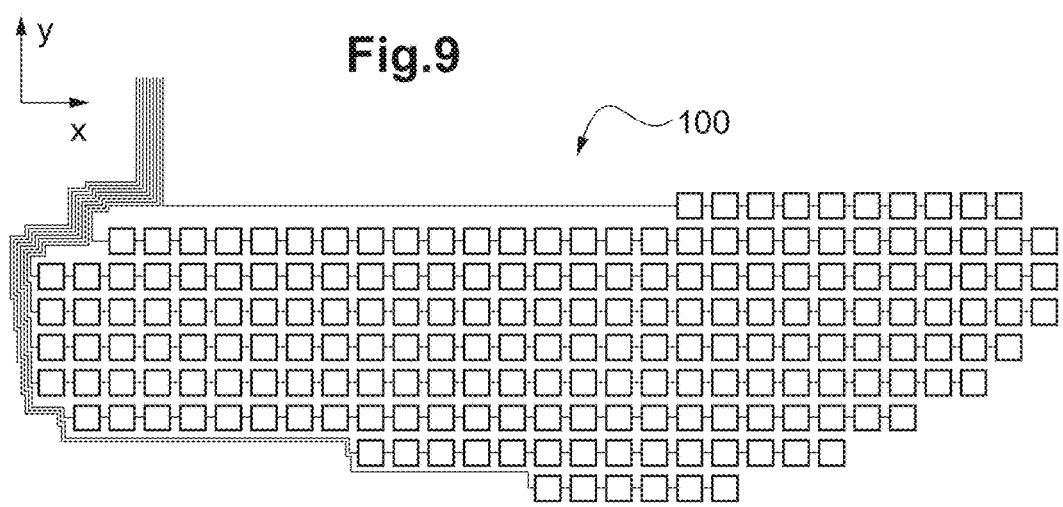
Figure 10:
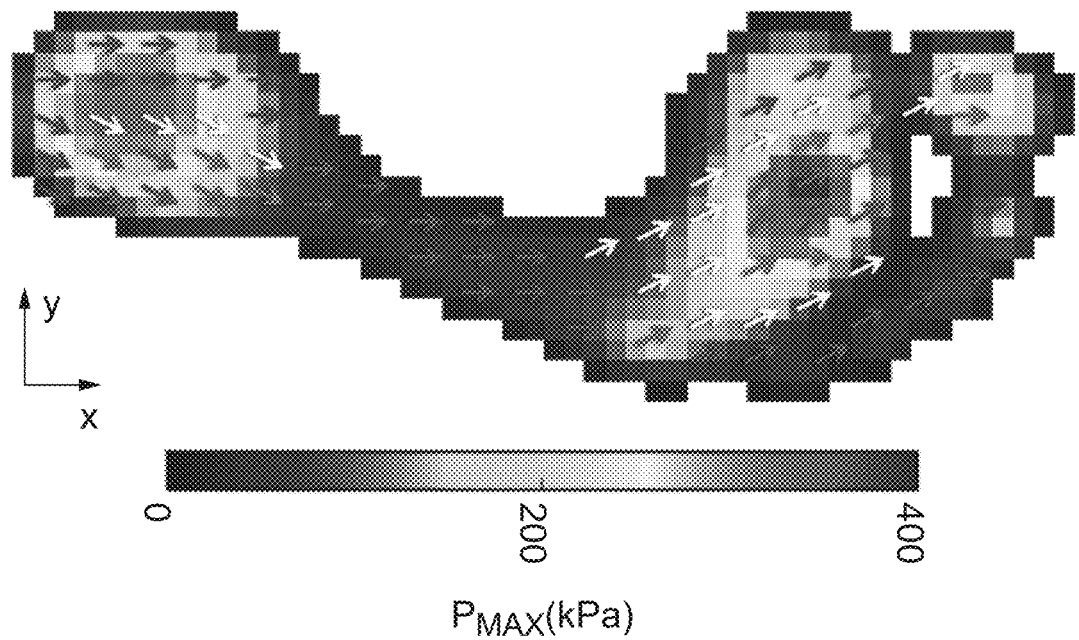
Figure 11:
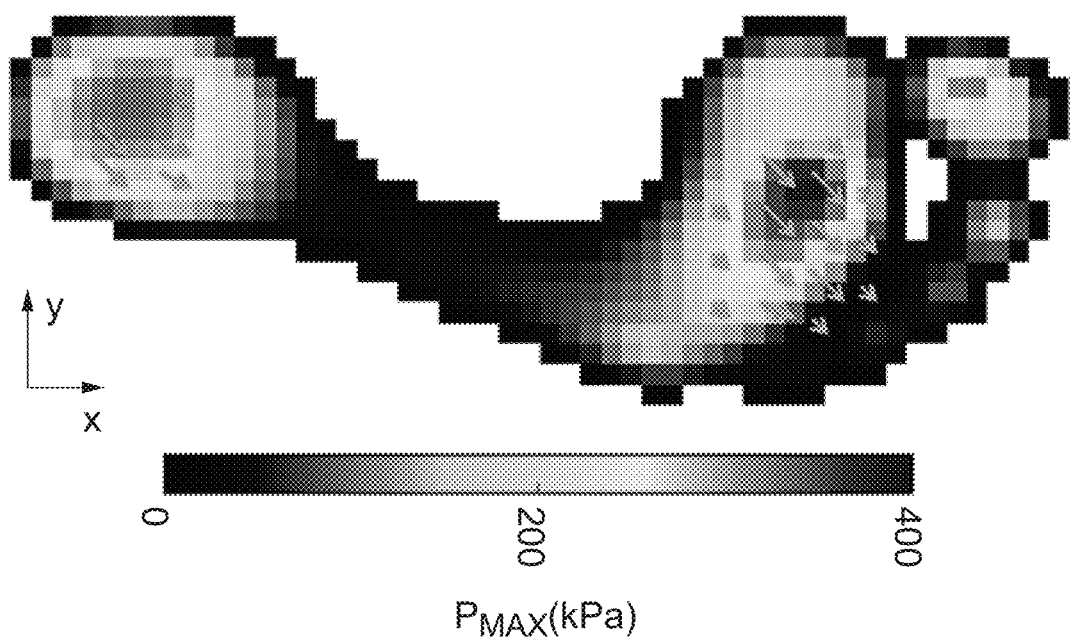
Figure 12:
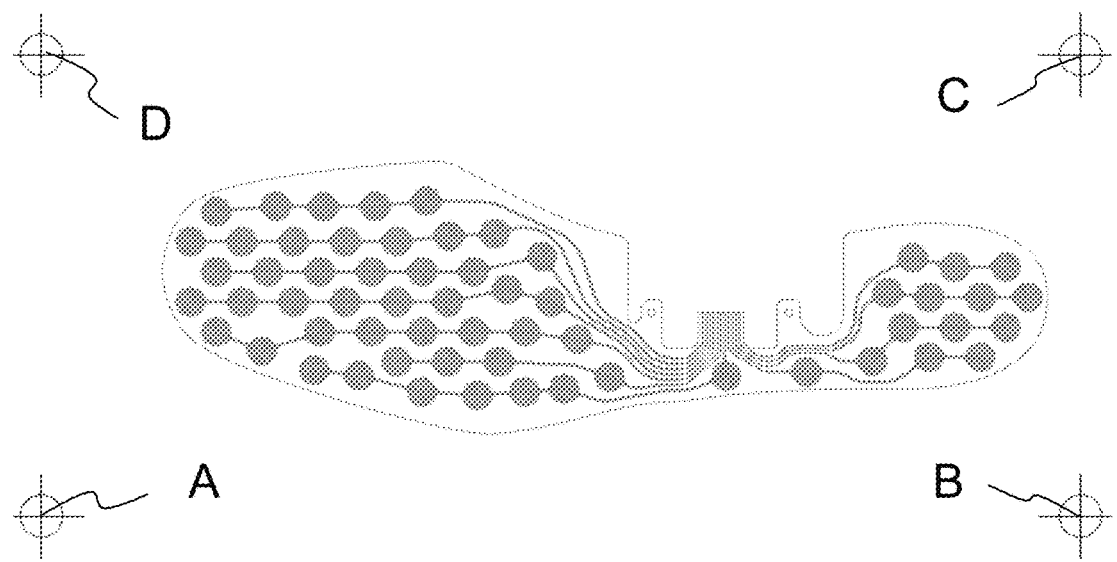
Figure 13:
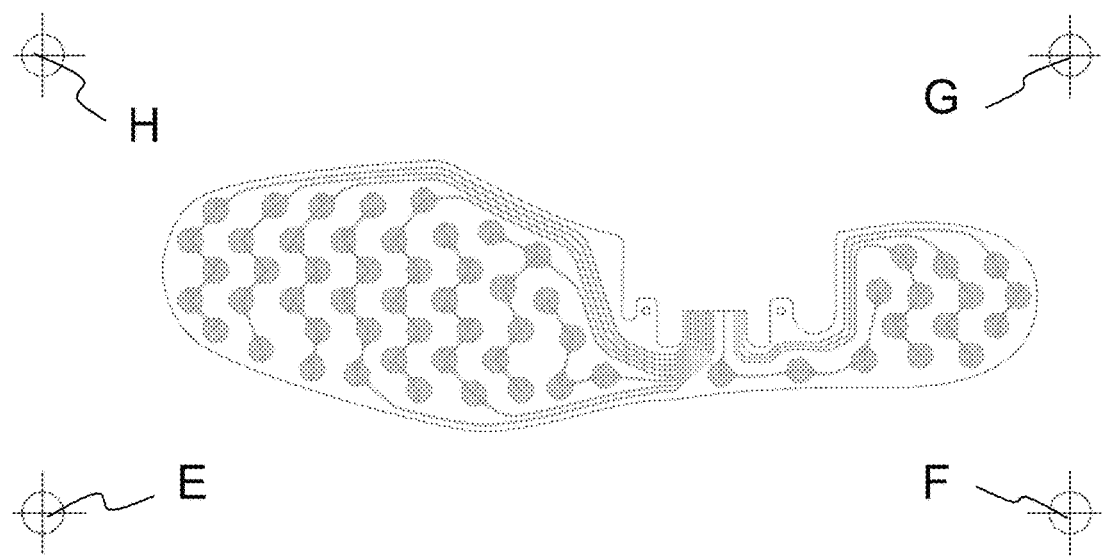

FIGS. 7-8 schematically show a top view of the electrodes of a matrix network of capacitive normal-pressure sensors, FIG. 7 corresponding to the electrodes fixed to one face of the dielectric and FIG. 8 corresponding to the electrodes fixed to the other face of the dielectric;

FIG. 9 schematically shows a bottom view of a shoe sole comprising a network of capacitive pressure sensors;

FIG. 10 illustrates a graphic representation of normal-pressure and shear-force measurements obtained with a sole with capacitive pressure sensors as shown in FIG. 9;

FIG. 11 illustrates another graphic representation of normal-pressure and shear-force measurements obtained with a sole with capacitive pressure sensors;

FIG. 12 illustrates a step of a method of manufacturing a sole with a network of capacitive pressure sensor cells after the printing by screen printing of a first pattern of electrodes;

FIG. 13 illustrates another step of a method of manufacturing a sole with a network of capacitive pressure sensor cells after the printing by screen printing of a second pattern of electrodes.

DEVICE

In FIG. 1 is shown, in top view, a capacitive pressure sensor cell according to an embodiment of the invention. More precisely, FIG. 1 shows in superimposition the drawing of the electrodes of a cell 20 of capacitive sensors. The electrodes are arranged on the opposite faces of a sheet of a dielectric material elastically deformable in compression and shear. An orthonormal reference system XYZ is also shown, the axis Z being perpendicular to the plane of FIG. 1.

In FIGS. 2-3 is shown a partial sectional view along the line AA of the capacitive sensor cell of FIG. 1. The axis Y of the orthonormal reference system XYZ is perpendicular to the plane of FIG. 2-3. In FIG. 2, the cell 20 is at rest. In FIG. 3 is shown the cell 20 under the effect of a force F having, generally, a component along the axis Z, also called normal force, and two components along the axes X and Y, also called shear forces.

The cell 20 includes a capacitive sensor 10 for sensing normal pressure in the direction Z, a capacitive sensor 30 for sensing the shear in the direction X and another capacitive sensor 50 for sensing the shear in the direction Y.

The capacitive sensor cell comprises a sheet of dielectric material 7 elastically deformable in compression and shear. Advantageously, the sheet of dielectric material 7 is formed of a sheet of elastomer material. Among the elastomeric materials, it can be mentioned in particular a elastomer of natural origin, the rubber, and synthetic elastomers, the silicones. The mechanical resilience of an elastomer material is defined as the ratio, often expressed in %, of the energy rendered after deformation, to the energy provided to deform the elastomer to under cyclic loading. The hysteresis corresponding to the rate of dissipated energy, the hysteresis is the complement of the mechanical resilience. A great resilience corresponds to a low hysteresis. Most of the elastomeric materials have a rather high mechanical resilience. However, the elastomer that has the highest resilience, hence the lowest hysteresis, in the natural rubber. Moreover, the natural rubber is cheap and has a good strength to abrasion. It is also observed a very low hysteresis of the pure soft silicones, i.e. not reinforced with particles. For example, the sheet of dielectric material 7 is formed of a sheet of natural rubber, silicone or urethane. For example, the sheet of dielectric material 7 is in the form of a closed-cell foam. Preferably, the sheet of dielectric material 7 has a Young's Modulus comprised between 1 and 5 MPa, adapted for the measurements of compression.

Advantageously, for the shear measurements, the sheet of dielectric material 7 has a Poisson module, defining his compressibility, comprised between 0 and 0.5 and preferably lower than 0.1. The determination of the value of the Poisson module results from a compromise: a value of 0.5 is ideal for a shear measurement but, in this case, the material is incompressible, the sensitivity in normal pressure is very low. An intermediate value of the Poisson module of about 0.2 allows a good sensitivity both in normal pressure measurement and in shear force measurement. Among the materials having a Poisson module of the order of 0.5, we find in particular the following materials: the butyl rubber, the polymer foams, the neoprene, the silicones, the polyurethane and the polyisoprene. To obtain a Poisson module lower than 0.5, we turn towards the micro-architectured materials. In particular, there exists a material that has, at the natural state, a null Poisson module (V=0): cork. The foams may also have a Poisson module comprised between 0.1 and 0.4. However, most of the foams settle down in compression.

Advantageously, the dielectric material has a dielectric constant comprised between 3 and 10 kV/mm.

Preferably, the thickness of the sheet of dielectric material 7 is comprised between 0.2 and 1 mm.

In the exemplary embodiment illustrated in FIG. 1, the cell 20 has a side of about 1 cm. The cell 20 includes electrodes 1, 2, 3, 4 arranged on the opposite faces of the sheet of dielectric material 7 to form capacitive sensors. Electrical tracks 11, 12, 13, 14, 15, 16 are connected to the different electrodes, as detailed hereinafter. In the example illustrated in FIGS. 2-3, a sheet 8, 9 of electrically insulating and flexible material is placed on each face of the sheet of dielectric material 7, respectively, in order to protect the electrodes 1, 2, 3, 4 and the conductive tracks 11, 12, 13, 14, 15, 16. The sheets 8, 9 are for example sheets of kapton of thickness comprised between 50 and 100 microns. The kapton has a dielectric constant of 110 kV/mm.

The first capacitive sensor 10 includes a first electrode 1 fixed to the first face of the sheet of dielectric material 7 and a second electrode 2 fixed to the second face of the sheet of dielectric material 7. In the example illustrated in FIG. 1, the first electrode 1 and the second to electrode 2 are square in shape. Other shapes of electrodes are conceivable, as described for example in relation with FIG. 4. Herein, the surface of the first electrode 1 is greater than the surface of the second electrode 2. In FIGS. 1 and 2, in the absence of shear forces in the direction X or Y, the extent of the surface of the first electrode 1 fully covers the extent of the surface of the second electrode 2. For example, the electrode 1 is a square of 5 mm side and the electrode 2 is a square of 4 mm side, centered to the electrode 1. In the absence of compressive force and shear force, the first electrode 1 is separated from the second electrode 2 by the sheet of dielectric material 7 of thickness L. Preferably, the thickness L is lower than 2 mm, for example the thickness L is comprised between 0.2 mm and 1.5 mm. The first electrode 1 is connected to an electrically conductive track 11 deposited on the first face of the dielectric material. Similarly, the second electrode 2 is connected to another electrically conductive track 12 deposited on the second face of the dielectric material. The first electrode 1 and the second electrode 2, separated by the dielectric material 7, define a capacitor, whose surface S12 is determined by the opposites surfaces of the first electrode 1 and the second surface 2. In this embodiment, at rest, the surface S12 is equal to the smallest of the surfaces of the two square electrodes 1, 2. In FIGS. 2 and 3, the vertical dash-lines between the electrodes 1 and 2 delimit the extent of the capacitor formed between these electrodes. The conductive tracks 11 and 12 are offset in the plane XY in order not to contribute to the value of measurement of the capacitor formed between the electrodes 1 and 2.

In the absence of pressure or shear force, the capacitance value of the first capacitive sensor 10 is determined by the thickness L of the dielectric 7 and by the surface S12, by application of the equation (I). When a compressive force is applied to the pressure sensor 10 in the direction Z, the thickness of the dielectric 7 varies by $\Delta L$, whereas the surface S12 remains constant. The capacitance of the capacitive sensor 10 hence varies as a function of the variation of thickness $\Delta L$ of the dielectric 7. The capacitive sensor 10 hence allows measuring the compressive force in the direction Z. In FIG. 3 is shown a sectional view of the pressure sensor along the section line AA following the application of a shear force F applied in the direction X to the first face of the dielectric 7. The shear force F induces a relative lateral displacement $\Delta X$ between the first face of the dielectric 7 and the second face of the dielectric 7 in the direction X. Simultaneously, the shear force F induced a compression $\Delta L$ of the thickness of the dielectric in the direction Z. However, the first electrode 1 being more extended than the second electrode 2, the opposite surface S12 of the electrodes 1 and 2 remains constant. Consequently, the first capacitive sensor 10 is only sensitive to the variation $\Delta L$ of thickness of the dielectric. A calibration of the capacitance value of the first capacitive sensor 10 hence allows deducing therefrom a measurement of the variation ΔL of thickness of the dielectric. This measurement is taken between the conductive tracks 11 and 12.

The second capacitive sensor 30 includes a first electrode 3 fixed to the first face of the sheet of dielectric material 7 and a second electrode 4 fixed to the second face of the sheet of dielectric material 7. In the example illustrated in FIG. 1, the first electrode 3 and the second to electrode 4 are comb-shaped, the comb teeth being arranged at equidistance along the direction X and extending along the direction Y. For example, the first electrode 3 and the second electrode 4 each comprise three teeth applied toing length along the direction Y. In FIG. 1, at rest, the teeth of the first electrode 3 are offset with respect to the teeth of the second electrode 4 in the direction X and partially overlap each other. The first electrode 3 is connected to an electrically conductive track 13 deposited on the first face of the dielectric material. The track 13 is connected to the first electrode 1 of the first pressure sensor 10. The second electrode 4 is connected to another electrically conductive track 14 deposited on the second face of the dielectric material. The first electrode 3 and the second electrode 4, separated by the dielectric material 7, defining a capacitor whose surface S34 is determined by the opposite surfaces of the first electrode 3 and the second electrode 4. The surface S34, defined by the intersection of the projection of the first electrode 3 to the second electrode 4, determines the surface of the capacitor formed by the electrodes 3 and 4 separated by the dielectric 7. In FIGS. 2 and 3, the vertical dash-lines between the electrodes 3 and 4 delimit the extent of the capacitor formed between these electrodes. The conductive tracks 13 and 14 are offset in the plane XY in order not to contribute to the measurement of the variation of capacitance of the capacitor formed between the electrodes 3 and 4. In the direction Y, the electrode 3 extends beyond the ends of the electrode 4. The shape and arrangement of the comb-shaped electrodes 3 and 4, with growing length teeth, allow maximizing the surface S34 for a minimum bulk of the sensor cell 20. The increase of the number of teeth allows increasing the accuracy of the measurements by increasing the value of the variation of surface ΔS34 for a same shear force value and reducing in relation the effect of the parasitic capacities.

The parasitic capacities may have several origins. Firstly, the sensor itself includes parasitic capacities formed between parallel conductive tracks. Indeed, two cupper conductive tracks, printed side by side, form a capacitance where the surface placed opposite is equal to the length of the conductive track multiplied by the thickness of the cupper layer. Secondly, parasitic capacities are introduced by the electronic circuit. Finally, another parasitic item is introduced at the time of an external contact, for example with a finger of the user, on the surface of the kapton. To remedy this situation, a shield, consisted of a cupper or aluminum plate, is arranged on each face external to the sensor.

In the absence of pressure or shear force, the value of capacitance of the second capacitance sensor 30 is determined by the thickness L of the dielectric 7 and by the surface S34, by application of the equation (I). When a compressive force is applied to the pressure sensor 30 along the direction Z, the thickness of the dielectric 7 varies by ΔL, whereas the surface S34 remains constant. The capacitance of the capacitive sensor 30 hence varies as a function of the variation of thickness ΔL of the dielectric 7.

As illustrated in FIG. 3, when a shear force is applied in the direction X to the first face of the dielectric 7, the pressure sensor 30 undergoes a relative lateral offset ΔX between the first electrode 3 and the second electrode 4 in the direction X. The lateral offset ΔX induces a to variation of the surface S34, which decreases when the shear force is applied in the direction of the positive Xs and increases when the shear force is applied in the direction of the negative Xs. However, even in the absence of compressive force component, a shear force induces, simultaneously with the lateral offset ΔX, a deformation of thickness ΔL of the elastically deformable dielectric material 7.

The measurement of the variation of electrical capacitance of the second capacitive pressure sensor 30 is hence sensitive both to a compressive force along the axis Z and to a shear force applied along the axis X. Nevertheless, the combination of the measurement of the first sensor 10 and of the measurement of the sensor 30 allows discriminating a normal pressure force from a shear force applied along the axis X.

On the other hand, when a shear force is applied along the axis Y, the surface S34 of the capacitive pressure sensor 30 remains invariable, due to the fact that the electrode 3 extends over a greater length than the electrode 4.

Hence, the second capacitive pressure sensor 30 is sensitive to a relative lateral offset along the axis X between the electrodes 3 and 4 and insensitive to a relative lateral offset along the axis Y between the electrodes 3 and 4. The capacitive pressure sensor 30 is also sensitive to a variation of thickness ΔL along the axis Z between the electrodes 3 and 4.

The measurement of the variations of capacitance value of the second capacitive sensor 30 is taken between the conductive track 11 and the conductive track 14. Indeed, the conductive track 11 is connected to the first electrode 1 of the first sensor 10, itself connected via the conductive track 13 to the electrode 3 to the second sensor 30.

Similarly and complementarily, the third capacitive sensor 50 includes a first electrode 5 fixed to the first face of the sheet of dielectric material 7 and a second electrode 6 fixed to the second face of the sheet of dielectric material 7. In the example illustrated in FIG. 1, the first electrode 5 and the second electrode 6 are comb-shaped, the comb teeth being arranged at equidistance along the direction Y and extending along the direction X. By way of illustrative and not-limitative example, the first electrode 5 and the second electrode 6 each comprise three teeth of growing length in the direction Y. In FIG. 1, at rest, the teeth of the first electrode 5 are offset with respect to the teeth of the second electrode 6 in the direction Y so as to partially overlap each other. The first electrode 5 is connected to an electrically conductive track 15 deposited on the first face of the dielectric material. The track 15 is connected to the first electrode 1 of the first pressure sensor 10. The second electrode 6 is connected to another electrically conductive track 16 deposited on the second face of the dielectric material. The first electrode 5 and the second electrode 6, separated by the dielectric material 7, define a capacitor whose surface S56 is determined by the opposite surfaces of the first electrode 5 and of the second electrode 6. More precisely, the surface S56 is defined by the intersection of the projection of the first electrode 5 to the second electrode 6. This surface S56 determines the surface of the capacitor formed by the electrodes 5 and 6 separated by the dielectric 7. The conductive tracks 15 and 16 are offset in order not to contribute to the measurement of the capacitance variation of the capacitor formed between the electrodes 5 and 6. In the direction X, the electrode 5 extends beyond the ends of the electrode 6. The shape and arrangement of the comb-shaped electrodes 5 and 6, with growing length teeth, allow maximizing the surface S56 for a minimum bulk of the sensor cell 20.

In the absence of pressure or shear force, the capacitance value of the third capacitive sensor 50 is determined by the thickness L of the dielectric 7 and by the surface S56, by application of the equation (I). When a compressive force is applied to the pressure sensor 50 along the direction Z, the thickness of the dielectric 7 varies by ΔL, whereas the surface S56 remains constant. The capacitance of the capacitive sensor 50 hence varies as a function of the variation of thickness ΔL of the dielectric 7.

When a shear force F is applied in the direction Y to the first face of the dielectric 7, the pressure sensor 50 undergoes a thickness deformation ΔL and a relative lateral offset ΔY between the first electrode 5 and the second electrode 6 in the direction Y. The lateral offset ΔY induces a variation of the surface S56, which decreases when the shear force is applied in the direction of the positive Ys and increases when the shear force is applied in the direction of the negative Ys. The displacement ΔY along the axis Y depends directly on the thickness L of the dielectric, of the Poisson coefficient V, of the Young's modulus E, of the force F applied along Y and of the surface area A to which this force is applied according to the following formula:

$$\Delta Y = 2(1+V)F*L/(E*A) \quad (II)$$

For example, with a silicone sheet, a variation of surface ΔS of the order of 10% is measured, for a shear force F of the order of 50 Newtons applied in the direction Y on a surface of 1 cm$^2$.

The measurement of the variation of electrical capacitance of the third capacitive pressure sensor 50 is hence sensitive both to a compressive force along the axis Z and to a shear force applied along the axis Y. Nevertheless, the combination of the measurement of the first sensor 10 and of the measurement of the third sensor 50 of a same cell allows discriminating a normal pressure force from a shear force applied along the axis Y.

On the other hand, when a shear force is applied along the axis X, the surface S56 of the capacitive pressure sensor 50 remains invariable, due to the fact that the electrode 5 extends over a greater length than the electrode 6.

Hence, the third capacitive pressure sensor 50 is sensitive to a relative lateral offset along the axis Y between the electrodes 5 and 6 and insensitive to a relative lateral offset along the axis X between the electrodes 5 and 6. The capacitive pressure sensor 50 is also sensitive to a variation of thickness ΔL along the axis Z between the electrodes 5 and 6.

The measurement of the variations of the capacitance value of the third capacitive pressure sensor 50 is taken between the conductive track 11 and the conductive track 16. Indeed, the conductive track 11 is connected to the first electrode 1 of the first sensor 10, itself connected via the conductive track 15 to the electrode 5 of third sensor 50.

The three sensors 10, 30 and 50 being arranged close to each other, the approximation is made that the variation of thickness ΔL is identical for the three sensors 10, 30, 50 of a same cell 20. The measurement of the three electrical capacitances of the first capacitive pressure sensor 10, the second capacitive pressure sensor 30 and the third capacitive pressure sensor 50, respectively, allows deducing therefrom the intensity and direction of a compressive force applied along the axis Z, of a shear force applied along the axis X and of a shear force applied along the axis Y. A cell 20 hence provides 6 information items.

For example, to measure the shear, the interesting value measured is C[X or Y]/C[normal], the component L, considered as identical for adjacent capacitances, in eliminated. Let's note C[X] the capacitance of the sensor 30, A[X] the effective surface of the sensor 30, C[Y] the capacitance of the sensor 50, A[Y] the effective surface of the sensor 50, and C[Normal] the capacitance of the sensor 10 and A[Normal] the effective surface of the sensor 10. By application of the formula (I), we obtain:

$$C[X] = \varepsilon * A[X]/L[X]$$

$$C[Normal] = \varepsilon * A[Normal]/L[Normal]$$

where ε represents the dielectric constant of the dielectric material 7.

It is considered that L[X]=L[Normal] because the sensors 10 and 30 are very close to each other, and the surface of the normal pressure sensor 10, A[Normal], is constant.

It is deduced therefrom that:

$$C[X]/C[Normal] = A[X]/A$$

The measurement of the variations of the ratio between the capacitance of the shear sensor 30 along the axis X and the capacitance of the normal pressure sensor 10 between an initial state and during the application of a force, allows deducing therefrom the value of ΔX. By application of the formula (II), it is deduced therefrom the measurement of the shear force F along the axis X.

The cell 20 of three capacitive sensors is connected to a system of measurement by only four electrically conductive tracks, the tracks 11, 12, 13 and 14. The track 11 is deposited on the first face of the dielectric 7, whereas the tracks 12, 14 and 16 are deposited on the second face of the dielectric 7. The opposite electrodes being on distinctive faces, a design of electrodes in a single plane may be used. This arrangement of the conductive tracks simplifies the method of manufacturing by comparison with the designs of multilevel electrodes, which require more manufacturing steps. In the prior art systems, two independent electrical tracks are generally used for each capacitive sensor, i.e. six tracks for three sensors. The arrangement of the cell 20 allows reducing the number of electrical tracks from and towards an electronic system of measurement.

The cell is connected to an electronic system of measurement via the conductive tracks 11, 12, 13, 14. The electrical capacitances of the first sensor 10, the second sensor 30 and the third sensor 50 are measured sequentially. Particularly advantageously, each track is measured with a frequency of 100 Hz.

A drawback of the configuration of the cell 20 is that the potential applied to the to electrode 1 risks not to be uniform over the whole surface of the electrodes 1, 3 and 5 connected in series, which potentially affects the accuracy of the measurements.

For a normal pressure force of 100 Newtons, the measured variation of the capacitance of the sensor 10 is of the order of 50%, compared to the measurement of the same capacitance at rest.

For a shear force of 50 Newtons along the axis X, the measured variation of capacitance of the sensor 30 is of the order of 10%, compared to the measurement of the same capacitance at rest.

The dielectric material is chosen as a function of the applications. The sheet of dielectric material must remain in its zone of elasticity for applied pressures comprised between 0 and 10 kg/cm$^2$ (corresponding to the means of the foot sole pressure) and the maximum compression must be lower than 50% when the pressure applied is of 10 kg/cm². Hence, when the capacitance at the output of the electrodes is measured, before and after the application of a pressure force, respectively, it is possible to calculate the variation of thickness of the dielectric material, for example silicone. By application of the Hook law, in the zone of elasticity of the material, it is deduced from the variation of thickness L a measurement of the pressure applied. Indeed, the Hook law indicates that the normal pressure a applied at the surface of the material is equal to the product of the Young's modulus E of the material by the percentage ΔL/L of thickness deformation of the material:

$$\sigma = E \cdot \Delta L / L \tag{III}$$

Preferably, a dielectric material elastically deformable in compression and shear, and which remains in its zone of elasticity for a normal pressure comprised between 0 and 10 kg/cm², is used. At the maximum pressure of 10 kg/cm², the compression of the material is preferably limited between 10% and 50% of the thickness. A range of theoretical values of Young's modulus comprised between 30 kg/cm² and 100 kg/cm² is defined. As regards the characteristics empirically determined, the dielectric material must have a tensile strength defined by the maximum pressure applied before break, comprised between 20 and 100 MPa.

In another exemplary embodiment, it is chosen as a dielectric 7 a sheet of urethane of 1 mm thick, provided by the Grainger company (https://www.grainger.com/product/Foam-Sheet-13C455?functionCode=P2IDP2PCP). The urethane foam especially suits for measuring the normal pressure. The urethane has the advantage to show a good compression, hence to allow a good spatial resolution of measurement. Moreover, the urethane has a low hysteresis.

In another exemplary embodiment, it is chosen as a dielectric 7 a sheet of polyurethane foam. This material has the advantage to show a very reduced hysteresis, about 6%. This material is in particular well suited to the applications to the measurement of essentially the normal pressure.

In FIG. 5 is shown a measurement of variation of capacitance C (in pF) as a function of a normal pressure force P (in N/cm²) applied to a pressure sensor according to an exemplary embodiment of the invention, by applying an increasing then decreasing pressure force. The to dielectric material is herein urethane. These measurements are a good illustration of the hysteresis effect of the sensor, which nevertheless remains limited to less than 7% for the urethane. This hysteresis effect may produce important uncertainties about the measurements, because the information for determining if we are on the increasing or the decreasing pressure curve is not available.

In another example, the dielectric 7 is made of polyurethane foam, of 1 mm thick. The polyurethane foam is especially well suited to the applications to the measurement of normal pressure forces.

In an exemplary embodiment, it is chosen as a dielectric 7 an elastomer, for example a sheet of silicone of 1 mm thick, having a hardness comprised between 10 and 20, of the Nusil trademark. The hardness is linked to Young's modulus E by an empiric relation. In another example, it is chosen as a dielectric 7 a sheet of silicone of 0.5 mm thick, for example of the Nusil company, reference MED 4901. The silicone is especially well suited to the applications to the measurement of shear forces. The drawback of the silicone is that it shows a high hysteresis, that is located around 30%.

In another exemplary embodiment, it is chosen as a dielectric 7 a sheet of cork that has the advantage to have an extremely low Poisson module (V=0).

The electrodes and the conductive tracks are for example deposited or printed on two ultra-thin sheets 8, 9 of kapton. A sheet 9 of kapton carrying the electrodes 1, 3, 5 and the conductive tracks 11, 13, 15 is stuck to a face of the sheet of dielectric 7. Another sheet 8 of kapton carrying the electrodes 2, 4, 6 and the conductive tracks 12, 14, 16 is stuck to the other face of the sheet of dielectric 7.

In FIG. 4 is shown a variant of a pressure sensor cell 20. The same signs of reference denote elements identical to those of FIG. 1. In particular, the structure and the operation of the sensors 30 and 50 are identical to those of the sensors described in relation with FIG. 1. In the variant of FIG. 4, the shape and size of the electrodes 1, 2 of the first pressure sensor 10 are different from those of the sensor 10 of the cell illustrated in FIG. 1. In the variant of FIG. 4, the first electrode 1 is formed of a square whose side length is lower than the size of the electrode 2. The electrode 2 is formed of two portions of electrodes connected in series. For example, the electrode 2 is formed of two rectangles separated by a trench extending along the direction X and connected in series by a conductive track. The surface of the first electrode 1 does not cover totally the surface of the second electrode 2. Herein, the surface of the first electrode is lower than the surface of the second electrode 2. The surface S12 of the capacitor formed by the dielectric between the electrodes 1 and 2 is herein consisted of two rectangles and not of a square. On the other hand, the conductive track 16 is not in the continuation of a rectangle of the comb of the electrodes 6. Nevertheless, the operation of the sensor 10 of FIG. 4 is similar to that of the sensor 10 of FIG. 1.

Generally, the electrodes 1 and 2 of the first sensor are configured so that, when the sensor 10 is subjected to a shear force along the direction X or Y, in the limit of the elastic to deformation of the dielectric material 7, the surface S12 remains constant. As it is obviously for the one skilled in the art, the structure and the shape of the electrodes 1 and 2 are interchangeable. Likewise, the electrodes 3 and 4 are interchangeable, as well as the electrodes 5 and 6.

In an exemplary embodiment, a sensor cell 20 occupies a square surface of 1 mm side. It is possible to integrate a great number of sensor cells 20 on a same sheet of dielectric material to form a high-spatial-resolution sensor network. The more little the surface of the cell is, the more the spatial resolution (number of sensors per cm²) increases. Nevertheless, we are limited by the thickness of the dielectric 7 presently available on the market. Indeed, if it is desired to reduce the size of the sensor, the surfaces S placed opposite to each other must be reduced, now the thickness L must be small with respect to the characteristic magnitude of S, so that the approximation of a plane capacitor can be made.

In FIG. 6 is shown in top view an example of a pressure sensor network. This network 100 comprises a set of pressure sensor cells 20, as described in relation with FIG. 1, these cells being arranged as a matrix on a same thin sheet of electrically deformable dielectric material 7. Particularly advantageously, the cells 20 are arranged in rows and columns.

In FIG. 6, as in FIG. 1, the electrodes and the conductive tracks of the network of pressure sensors are shown in projection. The network 100 comprises for example two rows and three columns of cells of several pressure sensors. For example, the electrodes are manufactured by a printed circuit technique (PCB) and the network is developed using an Eagle software. In this case, the cells 20 of a same network are preferably identical to each other. The structure of a cell 20 is identical to that described in relation with FIG. 1. Generally, a cell 20 includes electrodes 1, 3 and 5 on one face of the dielectric material 7 and electrodes 2, 4 and 6 on the other face of the dielectric material 7. The electrodes 1 and 2 form a capacitive normal-pressure sensor, sensitive to the variations of thickness ΔL of the dielectric material 7. The comb-shaped electrodes 3 and 4, offset relative to each other, form a capacitive shear-pressure sensor sensitive to a shear force applied along the direction X. The comb-shaped electrodes 5 and 6, offset relative to each other, form a capacitive shear-pressure sensor sensitive to a shear force applied along the direction Y. Advantageously, the electrode 1 is connected to the electrode 3 by a conductive track 13. Similarly, the electrode 1 is linked to the electrode 5 by a conductive track 15. Hence, a cell 20 of pressure sensor controlled by only four external conductive tracks allow providing six pressure information items, i.e. 3D pressure measurements, with indication of the direction of the pressure applied.

The network 100 herein includes several pressure sensor cells arranged in rows and columns.

A conductive track 1100 is connected to the electrode 1 of a first cell located at the intersection of a first row and a first column. This track 1100 is continued so as to electrically connect the electrode 5 of a pressure sensor cell to the electrode 1 of another cell, immediately adjacent in the same column. Hence, the electrodes 1, 3 and 5 of all the cells of the first column to are connected in series.

Similarly, another conductive track 1101 is connected to the electrode 1 of one cell in a second column of the network 100. This track 1101 is continued so as to connect electrically the electrode 5 of a pressure sensor cell to the electrode 1 of another cell immediately adjacent to the second column. Hence, the electrodes 1, 3 and 5 of all the cells 20 of the second column are connected in series.

Likewise, another conductive track 1102 is connected to the electrode 1 of a cell in a third column of the network 100. This track 1102 is continued so as to connect electrically the electrode 5 of a pressure sensor cell to the electrode 1 of another cell, immediately adjacent, of the third column. Hence, the electrodes 1, 3 and 5 of all the cells 20 of the third column are connected in series.

Moreover, another conductive track 1200 is connected to the electrode 2 of the first cell located at the intersection of the first row and the first column. This track 1200 is continued so as to connect electrically the electrode 2 of a pressure sensor cell to the electrode 2 of another cell, immediately adjacent on the first row, and so on. Hence, the electrodes 2 of all the cells of the first row are connected in series to the track 1200.

Another conductive track 1400 is connected to the electrode 4 of the first cell located at the intersection of the first row and the first column. This track 1400 is continued so as to connect electrically the electrode 4 of a pressure sensor cell to the electrode 4 of another cell, immediately adjacent on the first row, and so on. Hence, the electrodes 4 of all the cells of the first row are connected in series to the track 1400.

Similarly, another conductive track 1600 is connected to the electrode 6 of the first cell located at the intersection of the first row and the first column. This track 1600 is continued so as to connect electrically the electrode 6 of a pressure sensor cell to the electrode 6 of another cell, immediately adjacent on the first row, and so on. Hence, the electrodes 6 of all the cells of the first row are connected in series to the track 1600.

Likewise, on the second row, the electrodes 2 of all the cells of the second row are connected in series to the track 1201, the electrodes 4 of all the cells of the second row are connected in series to the track 1401 and the electrodes 6 of all the cells of the second row are connected in series to the track 1601.

It is hence obtained a network including six cells arranged in two rows and three columns, which is electrically connected to an external system of polarization and measurement through the conductive tracks 1100, 1101, 1102, 1200, 1400, 1600, 1201, 1401, 1601, i.e. in total 9 conductive tracks. Now, each sensor cell provides six measurements, i.e. in total 36 measurements for six cells.

Each cell of the sensor network 100 is addressed by selecting a row and a column. The electronic system is adapted to measure capacitances between 1 and 20 pF. The architecture of the network allows a very high density of capacitive pressure sensors, with a very reduced number of conductive tracks of link with an external system of measurement of capacitances. A to sensor network, each cell of 3 sensors of which occupies a surface of 1 cm side, has been tested with success. For normal pressure sensor only, the density may be increased up to 3 or 4 sensors per $cm^2$.

The arrangement of the sensors allows using all the available surface, and providing measurements of normal pressure and shear force with a good sensitivity and a good accuracy.

In FIG. 7 is shown an example of scheme of a network of electrodes 1 intended to be fixed to a first face of a sheet of dielectric material 7. The conductive tracks 1100, 1101, 1102, . . . , 1109 connect in series the electrodes 1 by columns. The network of electrodes 1 and conductive tracks 1100, 1101, 1102, . . . , 1109 is printed on a support 9, for example a printed circuit or a thin sheet of kapton of thickness comprised between 50 and 100 microns. An alternative to kapton is polyester, which has the advantage to be less expensive, but to show a lower resistance to heat (80° C. max). Marks A, B, C, D are printed simultaneously on the support 9, to allow the alignment of the electrodes with respect to the sheet of dielectric material 7, in accordance to the electrical scheme provided.

In FIG. 8 is shown a scheme of a network of electrodes 2 intended to be fixed to the opposite face of the dielectric material 7. The conductive tracks 1200, 1201, . . . , 1208, 1209 connect in series the electrodes 2 by rows. The network of electrodes 2 and of conductive tracks 1200, 1201, . . . , 1208, 1209 is printed on a support 8, for example a printed circuit or another thin sheet of kapton. Marks E, F, G, H are printed simultaneously on the support 8.

The support 9 is placed on one face of the dielectric material, then the support 8 is placed on the opposite face of the dielectric material 7, so as to align the mark C with the mark H, respectively the mark B with the mark E, the mark D with the mark G, and finally the mark A with the mark F.

In FIGS. 7 and 8, it is observed that, for a network of 10 rows and 10 columns, hence including 100 sensor cells, 20 conductive tracks are sufficient to perform sequentially all the pressure measurements. For a network of 100 three-dimensional pressure sensor cells, corresponding to 300 sensors, it is sufficient to connect the network by 40 conductive tracks to perform sequentially all the measurements of pressure in compression and shear.

The measurements of all the sensors of a sensor network are not performed simultaneously, contrary to the systems in which each sensor is addressed independently.

This network of sensors allows simultaneously increasing the density of pressure sensors, which allows obtaining a good spatial resolution, while limiting the number of conductive tracks towards the outside.

In FIG. 9 is schematically shown a network 100 of capacitive pressure sensors intended to form a sole. The network includes 188 sensors arranged in 29 rows and 9 columns in the plane XY. The sensors are arranged according to a predetermined scheme corresponding to the general shape of a foot.

FIG. 10 schematically illustrates an example of graphical representation of the measurements of pressure obtained by means of a sole with sensors, as shown in FIG. 9. In to FIG. 10, the normal pressure measurement is represented by squares, which correspond to the spatial resolution of the sole. A color code allows representing the distribution of the values of normal pressure in the direction Z measured as a function of the XY position of the sensor. The shear force measurement is represented simultaneously in FIG. 10 by arrows: the direction of the arrows represents the direction of the shear force, resulting from the measurement of the shear force in the direction X and in the direction Y. The intensity of the shear force measurement is represented herein using a color code for the arrows.

FIG. 11 schematically illustrates another example of graphical representation of the measurements of pressure obtained by means of a sole with sensors, as shown in FIG. 9. The normal pressure measurements are shown similarly to FIG. 10, by squares whose color is coded as a function of the amplitude of the compressive force in the direction Z measured as a function of the XY position. The shear force measurement is represented simultaneously in FIG. 11 by arrows: the direction of the arrows represents the direction of the shear force, resulting from the measurement of the shear force in the direction X and in the direction Y. The length of the arrows herein represents the intensity of the shear force measurement.

The graphic representation of the pressure measurements provides to the user the distribution of the pressure forces over the surface of the sensor with a resolution of several tenths of sensors on a sole. The sensor provides for each elementary sensor, the intensity, the direction and the orientation of the force applied to the center of each sensor cell, hence the interest to have a maximum of sensors and the finest possible spatial resolution. The sensor network allows determining accurately the point of application of the pressure force.

The representation of the pressure measurements illustrated in FIGS. 10 and 11 allows immediately to a user with no particular qualification to know the spatial distribution of the pressure forces on the sensor network sole.

The measurements may be repeated at a high frequency, which allows correcting a bad posture.

In the medical field, a sensor network integrated to a sole finds in particular applications as a diagnostic tool for foot specialists (podologists, pedorthists . . . ), as a tool for physical recovery aid, or as a prevention sole daily worn by a diabetic patient suffering from neuropathy. A pressure sensor network may be integrated to a carpet as a diagnostic tool for the podologist. Integrated into a cloth or a garment, over a wider surface, the sensor network system may be used as a sheet for preventing eschars for handicapped persons. Placed on the handrails of the wheelchairs, a sensor network system allows quantifying the interaction with the hands of the hemiplegics. The detection of the bearing point of the body or the foot of a patient and the measurement of the pressure forces distribution may allow improving the prevention of eschars or the prevention of the foot injuries for the persons suffering from diabetes.

A sensor network sole may also find applications as a measurement tool for the vendors of personalized shoes (sportsman, luxury shoes . . . ).

Particularly advantageously, the sensor network system is wirelessly connected to a to control box.

In the sport field, a sensor network sole carried by a sportsman allows the latter to quantify his run.

The applications of the invention are not limited to applications in the medical or sport field, the pressure measurement sensors can today be connected to a smartphone and find application of self-measurement intended to the general public.

In the entertainment field, a pressure sensor network sole can be connected to a video game to replace a gamepad.

Other entertainment applications are contemplated, such as a connected dance mat, or a shock detector on the American football helmets.

Method

Various methods of manufacturing are contemplated for manufacturing a pressure sensor network within the framework of the invention.

In a first embodiment, the conventional technology of the printed circuits (PCB), preferably on flexible support (FPCB), is used. According to this technique, the electrodes are manufactured on electrically insulating supports 8 and 9, which are then fixed to the opposite faces of a sheet of dielectric material 7. Preferably, the electrodes and the conductive tracks are made of cupper or silver.

As indicated hereinabove, for each support, the manufacturing technique is based on a single level of electrodes. The manufacturing of the conductive tracks on a single level is rapid and produces an electrical circuit that is more reliable than an electrical circuit having several levels connected by vias. This advantage is decisive in the aimed applications in which the sensor network is subjected to relatively high compressive and/or shear forces, by comparison to tactile applications.

It is hence obtained a system including a thin sheet of dielectric 7 in sandwich between two flexible supports 8 and 9, the electrodes being fixed to the opposite faces of the dielectric and protected by the flexible supports 8, 9.

A wired or wireless link allows connecting electrically the conductive tracks of the sensor network to an external measurement system.

In another embodiment, the electrodes and conductive tracks are printed directly on a thin sheet of dielectric material. For that purpose, a metal ink printer (such as, for example, the Fujifilm Dimatix Materials Printer DMP-2800 Series) is used to print the electrodes 1, 3, 5 and the conductive tracks 11, 13, 15, 1100, 1101, . . . 1109 on a first face of the dielectric material, then the other electrodes 2, 4, 6 and the other conductive tracks 12, 14, 16, 1200, 1201, . . . 1209, 1400, . . . , 1600, 1601, . . . , may be printed on the other face of the dielectric material. Preferably, a metal ink composed of cupper or silver is used. By way of example, the ink is a silver ink of the Inktec company, reference TEK-IJ-020, composed of 20% in weight of silver. This method is faster than the method using a PCB. Currently less accurate than a PCB method but still rather expensive, it is highly probable that the cost of the metal ink print technique decreases and that the accuracy of the metal ink print gets far better in the next years.

In another embodiment, illustrated in FIGS. 12 and 13, it is manufactured a sole including only pressure sensors. The electrodes and the conductive tracks are printed by single-layer screen printing on a thin layer of PET having a thickness of about 100 microns. The first electrodes are printed as shown in FIG. 12 and the second electrodes are printed as shown in FIG. 13.

In an exemplary embodiment, the first electrodes and the second electrodes are printed in two adjacent areas on a same PET sheet. In this case, the first electrodes and the second electrodes may be printed simultaneously. In the vicinity of each electrode pattern, cross-shaped marks allowing the alignment of the electrode patterns are also printed on the PET sheet.

The PET sheet is cut so as to separate, on the one hand, the pattern of the first electrodes and, on the other hand, the pattern of the second electrodes. In another exemplary embodiment, the first electrodes and the second electrodes are printed on two distinct PET sheets, respectively.

A PET sheet carrying the pattern of the first electrodes is stuck to one face of a sheet of elastically deformable dielectric material, for example a polyurethane elastomer foam having a thickness of about 1 mm. Another PET sheet carrying the pattern of the second electrodes is stuck to the other face of the sheet of polyurethane elastomer foam. Advantageously, the sheet of polyurethane elastomer foam includes openings allowing the cross-shaped marks arranged on the sheet carrying the first electrodes to be aligned with the cross-shaped marks arranged on the sheet carrying the second electrodes. Hence, an initial alignment of the first and second electrode of each pressure sensor is obtained. After drying of the glue, the external shape of the sole is cut.

In the example illustrated in FIGS. 12-13, the sole includes 60 pressure sensors. The first electrodes are connected in series by 11 rows forming 11 conductive tracks intended to be connected to an electronic system. The second electrodes are connected in series by 12 columns forming 12 conductive tracks intended to be connected to an electronic system. Each pressure sensor represented by a disk is at the intersection of a row and a column, hence allowing the addressing of each of the 60 pressure sensors individually. The system is connected only by a total of 11+12=23 conductive rows. This sole hence offers a pressure sensor network having a high density and spatial resolution, while limiting the number of electrical connections.

In another exemplary embodiment, a sole of sensors is manufactured, including 69 pressure sensors, arranged in 11 rows and 16 columns, hence including in total only 27 electrical links.

Of course, the arrangements of the pressure sensors, of the rows and of the columns may be varied at will, to be adapted to the size of the foot and to the specific needs.

The invention claimed is:

1. A pressure sensor network system, comprising:
a sheet of dielectric material elastically deformable in compression and shear, the sheet of dielectric material having a first face and a second face;
a network comprising a plurality of pressure sensor cells, the cells being arranged in at least three rows and at least three columns, each cell comprising a first capacitive sensor for sensing normal pressure in a first direction (Z),
each capacitive sensor having a first electrode fixed to the first face of the sheet of dielectric material and a second electrode fixed to the second face of the sheet of dielectric material,
said first electrode of the capacitive normal-pressure sensor of a cell being connected in series to a first electrically conductive track connecting a row of cells of the sensor network, and
the second electrode of the capacitive normal-pressure sensor of a cell being connected to a second electrically conductive track connecting a column of capacitive normal-pressure sensors of the sensor network; and
addressing means adapted to measure the electrical capacitance of a capacitive sensor located at the intersection of a row and a column, said row corresponding to a first track connected to said first electrode and said column corresponding to another track connected to one of said second electrodes,
wherein at least one cell of the sensor network includes a second capacitive sensor for sensing shear in a second direction (X) and a third capacitive sensor for sensing shear in a third direction (Y),
each capacitive shear sensor having a first electrode fixed to the first face of the sheet of dielectric material and a second electrode fixed to the second face of the sheet of dielectric material, said first and second electrodes of the capacitive shear sensors being comb-shaped,
said first electrodes of the capacitive sensors of a cell being connected in series, the second electrode of the capacitive sensor for sensing shear in the second direction (X) being connected to a third electrically conductive track connecting a row of capacitive sensors for sensing shear in the second direction (X) of the sensor network, and
the second electrode (6) of the capacitive sensor for sensing shear in the third direction (Y) being connected to a fourth electrically conductive track connecting a column of capacitive sensors for sensing shear in the third direction (Y) of the sensor network.

2. The pressure and shear sensor network system according to claim 1, wherein the sheet of dielectric material elastically deformable in compression and shear is a material selected from the group consisting of: a micro-architectured cork, an elastomer, a rubber, a urethane, a silicone, a butyl rubber, a polymer, a neoprene, a polyurethane, a polyisoprene, and an urethane foam.

3. The pressure and shear sensor network system according to claim 2, wherein said first electrically conductive track and the second electrically conductive track of a cell are connected to an electronic system adapted to measure a variation of the electrical capacitance of the capacitive normal-pressure sensor, the electronic system being adapted to deduce therefrom a normal pressure force applied to said capacitive normal-pressure sensor along the first direction (Z).

4. The pressure sensor network system according to claim 2, wherein at least one cell of the sensor network comprises a second capacitive sensor for sensing shear in a second direction (X) and a third capacitive sensor for sensing shear in a third direction (Y), each capacitive shear sensor being consisted of a first electrode fixed to the first face of the sheet of dielectric material and a second electrode fixed to the second face of the sheet of dielectric material, said first and second electrodes of the capacitive shear sensors being comb-shaped, said first electrodes of the capacitive sensors of a cell being connected in series, the second electrode of the capacitive sensor for sensing shear in the second direction (X) being connected to a third electrically conductive track connecting a row of capacitive sensors for sensing shear in the second direction (X) of the sensor network; and the second electrode (6) of the capacitive sensor for sensing shear in the third direction (Y) being connected to a fourth electrically conductive track connecting a column of capacitive sensors for sensing shear in the third direction (Y) of the sensor network.

5. The pressure and shear sensor network system according to claim 1, wherein said first electrode and said first electrically conductive track are printed on a sheet of electrically insulating and flexible material, and, respectively, wherein said second electrode and said other electrically conductive tracks are printed on another sheet of electrically insulating and flexible material.

6. The pressure sensor network system according to claim 5, wherein at least one cell of the sensor network comprises a second capacitive sensor for sensing shear in a second direction (X) and a third capacitive sensor for sensing shear in a third direction (Y), each capacitive shear sensor being consisted of a first electrode fixed to the first face of the sheet of dielectric material and a second electrode fixed to the second face of the sheet of dielectric material, said first and second electrodes of the capacitive shear sensors being comb-shaped, said first electrodes of the capacitive sensors of a cell being connected in series, the second electrode of the capacitive sensor for sensing shear in the second direction (X) being connected to a third electrically conductive track connecting a row of capacitive sensors for sensing shear in the second direction (X) of the sensor network; and the second electrode (6) of the capacitive sensor for sensing shear in the third direction (Y) being connected to a fourth electrically conductive track connecting a column of capacitive sensors for sensing shear in the third direction (Y) of the sensor network.

7. The pressure and shear sensor network system according to claim 1, wherein the first electrically conductive track and the second electrically conductive track of a cell are connected to an electronic system adapted to measure a variation of the electrical capacitance of the capacitive normal-pressure sensor, the electronic system being adapted to deduce therefrom a normal pressure force applied to said capacitive normal-pressure sensor along the first direction (Z).

8. The pressure sensor network system according to claim 7, wherein at least one cell of the sensor network comprises a second capacitive sensor for sensing shear in a second direction (X) and a third capacitive sensor for sensing shear in a third direction (Y), each capacitive shear sensor being consisted of a first electrode fixed to the first face of the sheet of dielectric material and a second electrode fixed to the second face of the sheet of dielectric material, said first and second electrodes of the capacitive shear sensors being comb-shaped, said first electrodes of the capacitive sensors of a cell being connected in series, the second electrode of the capacitive sensor for sensing shear in the second direction (X) being connected to a third electrically conductive track connecting a row of capacitive sensors for sensing shear in the second direction (X) of the sensor network; and the second electrode (6) of the capacitive sensor for sensing shear in the third direction (Y) being connected to a fourth electrically conductive track connecting a column of capacitive sensors for sensing shear in the third direction (Y) of the sensor network.

9. The pressure sensor network system according to claim 1, wherein the first electrically conductive track and the third electrically conductive track of a cell are connected to said electronic system, which is adapted to measure a variation of the electrical capacitance of the second capacitive sensor for sensing shear in the second direction (X), the electronic system being adapted to deduce therefrom the amplitude and direction of a shear force applied to said capacitive sensor for sensing shear along the second direction (X).

10. The pressure sensor network system according to claim 1, wherein the first electrically conductive track and the fourth electrically conductive track of a cell are connected to said electronic system, which is adapted to measure a variation of the electrical capacitance of the third capacitive sensor for sensing shear in the third direction (Y), the electronic system being adapted to deduce therefrom the amplitude and direction of a shear force applied to said third capacitive shear sensor along the third direction (Y).

11. The pressure sensor network system according to claim 1, wherein said electrically conductive tracks are connected to means for measuring a variation of electrical capacitance of the capacitive sensors by wired or wireless links.

12. The pressure sensor network system according to claim 1, further comprising:
 a device for displaying pressure and/or shear force measurements,
 wherein the display device is configured to represent graphically, as a function of the arrangement of the sensor network, the normal pressure measured by each cell of the sensor network and/or simultaneously the amplitude and direction of the shear force measured by each cell of the sensor network.

13. A shoe sole comprising a pressure sensor network system according to claim 1.

\* \* \* \* \*